(12) United States Patent
Richter et al.

(10) Patent No.: US 9,458,097 B2
(45) Date of Patent: Oct. 4, 2016

(54) PROCESS FOR THE PREPARATION OF POLYISOCYANATES AND USE THEREOF

(71) Applicant: Bayer MaterialScience AG, Leverkusen (DE)

(72) Inventors: Frank Richter, Leverkusen (DE); Martin Brahm, Odenthal (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 14/509,202

(22) Filed: Oct. 8, 2014

(65) Prior Publication Data
US 2015/0025268 A1 Jan. 22, 2015

Related U.S. Application Data

(62) Division of application No. 13/193,189, filed on Jul. 28, 2011, now abandoned.

(30) Foreign Application Priority Data

Aug. 3, 2010 (DE) .................. 10 2010 038 845

(51) Int. Cl.
| | |
|---|---|
| C07C 263/16 | (2006.01) |
| C07D 273/04 | (2006.01) |
| C07D 251/34 | (2006.01) |
| C07F 9/54 | (2006.01) |
| C08G 18/02 | (2006.01) |
| C08G 18/16 | (2006.01) |

(52) U.S. Cl.
CPC ........... *C07C 263/16* (2013.01); *C07F 9/5435* (2013.01); *C08G 18/022* (2013.01); *C08G 18/168* (2013.01)

(58) Field of Classification Search
None
See application file for complete search history.

(56) References Cited

U.S. PATENT DOCUMENTS

| | | | |
|---|---|---|---|
| 4,960,848 A | 10/1990 | Scholl et al. | |
| 5,013,838 A | 5/1991 | Scholl | |
| 5,914,383 A | 6/1999 | Richter et al. | |
| 6,090,939 A | 7/2000 | Richter et al. | |
| 6,107,484 A * | 8/2000 | Richter | C07D 251/34 528/51 |

FOREIGN PATENT DOCUMENTS

| | | |
|---|---|---|
| CA | 2244486 A1 | 2/1999 |
| EP | 235388 A2 | 9/1987 |
| EP | 295926 A2 | 12/1988 |
| EP | 315692 A1 | 5/1989 |
| EP | 0339396 A1 | 11/1989 |
| EP | 379914 A2 | 8/1990 |
| EP | 447074 A2 | 9/1991 |
| EP | 0798299 A1 | 10/1997 |
| EP | 0896009 A1 | 2/1999 |
| EP | 962454 A1 | 12/1999 |
| EP | 962455 A1 | 12/1999 |
| EP | 0962455 A1 | 12/1999 |
| EP | 1645577 A1 | 4/2006 |
| WO | WO-02/48230 A1 | 6/2002 |
| WO | WO 02/48230 A1 | 6/2002 |

OTHER PUBLICATIONS

Search Report dated Oct. 26, 2011, in European Application No. EP—11176123.
Grim et al., (Zeitschrift fuer Naturforschung, Teil B: Anorganische Chemie, Organische Chemie, Biochemie, Biophysik, Biologie (1971), 26 (3), 184-90).
Beaumont et al., Journal of Fluorine Chemistry, 108(2001), 47-80.
He et al., Angew Chem. Int. Ed., 2008, 47, 9466-9468.
Dobrota et al., Eur. J. Org. Chem., 2008, 2439-2445.

* cited by examiner

*Primary Examiner* — Yun Qian
(74) *Attorney, Agent, or Firm* — Drinker Biddle & Reath LLP

(57) ABSTRACT

The invention relates to a process for isocyanate modification which includes reacting a) at least one organic isocyanate having an NCO functionality greater than or equal to 1, b) a catalyst comprising at least one phosphonium salt comprising at least one cycloalkyl substituent bonded directly to a P atom of a phosphonium cation, c) optionally a solvent, and d) optionally additives. The present invention also relates to a catalyst for isocyanate modification comprising at least one phosphonium salt comprising at least one cycloalkyl substituent bonded directly to a P atom of a phosphonium cation.

10 Claims, No Drawings

PROCESS FOR THE PREPARATION OF POLYISOCYANATES AND USE THEREOF

RELATED APPLICATIONS

This application is a division of U.S. patent application Ser. No. 13/193,189, filed Jul. 28, 2011, which claims benefit of German Patent Application No. 10 2010 038845.9, filed Aug. 3, 2010.

BACKGROUND OF THE INVENTION

The invention relates to the use of specific phosphonium salts as catalysts for isocyanate modification (oligomerisation or polymerisation), and to a process for the preparation of correspondingly modified isocyanates.

The oligomerisation or polymerisation of isocyanates, referred to here in summary as isocyanate modification, has been known for a long time. If the modified polyisocyanates contain free NCO groups, which may optionally also have been temporarily deactivated with blocking agents, they are extraordinarily high-quality starting materials for the production of a large number of polyurethane plastics and coating compositions.

A number of industrial processes for isocyanate modification have become established, in which the isocyanate to be modified, in most cases a diisocyanate, is generally converted by addition of catalysts and then, when the desired degree of conversion of the isocyanate to be modified has been reached, the catalysts are rendered inactive (deactivated) by suitable measures and the resulting polyisocyanate is generally separated from the unconverted monomer. A compilation of these processes of the prior art is to be found in H. J. Laas et al., *J. Prakt. Chem.* 1994, 336, 185 ff.

Compounds having an ionic structure have proved to be successful as modification catalysts, because they can be used in a very small amount and yield the desired result extremely quickly.

The possibility of using also tetraorganylphosphonium as cation to the anion having catalytic activity in respect of isocyanates, such as hydroxide, alkanoate, alkoxylate, etc., is generally known, although it is generally not explicitly given prominence as being particularly preferred, see: H. J. Laas et al., *J. Prakt. Chem.* 1994, 336, 185 ff.

Furthermore, the use of (hydrogen poly)fluorides, optionally also in the form of their phosphonium salts, for isocyanate modification is known inter alia from EP-A 962455, EP-A 962454, EP-A 896009, EP-A 798299, EP-A 447074, EP-A 379914, EP-A 339396, EP-A 315692, EP-A 295926 and EP-A 235388.

However, when the modification reaction is carried out, the tetraorganylphosphonium (hydrogen poly)fluorides of the prior art exhibit the disadvantage that occasionally, when they are used, the reaction can be maintained only by the continuous metered addition of catalyst, that is to say the decomposition of the catalyst in the isocyanate medium takes place unacceptably quickly in technical terms as compared with the modification reaction.

BRIEF SUMMARY OF THE INVENTION

The object underlying the invention was to develop a modification process using phosphonium salts as catalysts which is not to be encumbered with the above-mentioned disadvantages.

This has been possible by the provision of the process according to the invention.

In one embodiment, the invention provides a catalyst for isocyanate modification comprising phosphonium salts containing at least one cycloalkyl substituent bonded directly to the P atom of the phosphonium cation.

Another embodiment of the present invention is a process for isocyanate modification which comprises reacting
a) at least one organic isocyanate having an NCO functionality greater than or equal to 1,
b) a catalyst comprising at least one phosphonium salt comprising at least one cycloalkyl substituent bonded directly to a P atom of a phosphonium cation,
c) optionally a solvent, and
d) optionally additives.

Preferred phosphonium salts for isocyanate modification are those whose cation corresponds to the general formula I:

Formula I wherein $R_1$ to $R_4$ independently of one another represent identical or different, optionally branched and/or substituted organic radicals from the group $C_1$- to $C_{20}$-alkyl, $C_3$- to $C_{20}$-cycloalkyl, $C_7$- to $C_{20}$-aralkyl and $C_6$- to $C_{20}$-aryl, with the proviso that at least one of the radicals $R_1$ to $R_4$ represents an optionally branched and/or substituted $C_3$- to $C_{20}$-cycloalkyl radical, and a carbon atom of the cycloalkyl ring is bonded directly to the P atom.

Preferred cations of formula I are those in which $R_1$ to $R_4$ independently of one another represent identical or different organic radicals from the group $C_1$- to $C_{20}$-alkyl, cyclopentyl and cyclohexyl, wherein the alkyl radicals can be branched and the cycloalkyl radicals can be substituted, with the proviso that at least two of the radicals $R_1$ to $R_4$ represent an optionally substituted cyclopentyl and/or cyclohexyl radical and these are each bonded directly to the P atom via a ring carbon atom.

Particularly preferred phosphonium salts for isocyanate modification are those of the above-mentioned type wherein the following species are used as anions $X^-$ to the phosphonium cation of the general formula (I): fluoride ($F^-$), di- and/or poly-(hydrogen) fluorides ($[F^- \times (HF)_m]$, wherein m represents whole or fractional numbers from 0.001 to 20, preferably from 0.1 to 20, particularly preferably from 0.5 to 20, most particularly preferably from 0.5 to 5.

The catalysts can be used individually or in arbitrary mixtures with one another.

Another embodiment of the invention further provides a process for isocyanate modification, in which
a) at least one organic isocyanate having an NCO functionality ≥1,
b) a catalyst containing at least one phosphonium salt to be used according to the invention,
c) optionally solvents and
d) optionally additives
are reacted.

The modification process according to the invention very generally yields, in a simple manner, a broad range of polyisocyanates which are of high quality and are therefore very valuable for the polyurethane sector. Depending on the starting (di)isocyanate used, the process according to the invention yields polyisocyanates of the so-called isocyanate trimer type (i.e. containing isocyanurate and/or iminooxadiazinedione structures) with a small proportion of uretdione groups (isocyanate dimers). The proportion of the latter in the process products increases as the reaction temperature rises.

DETAILED DESCRIPTION OF THE INVENTION

For carrying out the process according to the invention, any known mono-, di- or poly-isocyanates of the prior art can in principle be used, individually or in arbitrary mixtures with one another.

Examples which may be mentioned include: hexamethylene diisocyanate (HDI), 2-methylpentane-1,5-diisocyanate, 2,4,4-trimethyl-1,6-hexane diisocyanate, 2,2,4-trimethyl-1,6-hexane diisocyanate, 4-isocyanatomethyl-1,8-octane diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI), 2,4- and 2,6-toluene diisocyanate (TDI), bis(4-isocyanatophenyl)methane (4,4'MDI), 4-isocyanatophenyl-2-isocyanatophenylmethane (2,4'MDI) as well as polynuclear products which are obtainable by formaldehyde-aniline polycondensation and subsequent conversion of the resulting (poly)amines into the corresponding (poly)isocyanates (polymer MDI).

The use of aliphatic, cycloaliphatic or araliphatic di- or poly-isocyanates having a functionality ≥2 is preferred.

The use of aliphatic, cycloaliphatic or araliphatic diisocyanates is particularly preferred.

Hexamethylene diisocyanate (HDI), 2-methylpentane-1, 5-diisocyanate, 2,4,4-trimethyl-1,6-hexane diisocyanate, 2,2,4-trimethyl-1,6-hexane diisocyanate, 4-isocyanatomethyl-1,8-octane diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI) are most particularly preferred.

It is irrelevant by which process the above-mentioned isocyanates are generated, that is to say with or without the use of phosgene.

The amount of catalyst to be used in the process according to the invention is governed primarily by the isocyanate used and the desired rate of reaction and is in the range from 0.001 to 5 mol %, based on the sum of the amounts of the isocyanate used and of the catalyst. Preferably from 0.002 to 2 mol % catalyst are used.

The catalyst can be used in the process according to the invention undiluted or dissolved in solvents. Suitable solvents are any compounds that do not react with the catalyst and are capable of dissolving it to a sufficient degree, for example aliphatic or aromatic hydrocarbons, alcohols, ketones, esters as well as ethers. Alcohols are preferably used.

The process according to the invention can be carried out in the temperature range from 0° C. to +250° C., preferably from 20 to 180° C., particularly preferably from 40 to 150° C., and can be terminated at any desired degree of conversion, preferably after from 5 to 80%, particularly preferably from 10 to 60%, of the monomeric diisocyanate used have been converted.

For deactivating the catalyst for the purpose of terminating the reaction, a whole number of prior-described methods of the prior art are possible in principle, such as, for example, the addition of (sub- or super-) stoichiometric amounts of acids or acid derivatives (e.g. benzoyl chloride, acid esters of phosphorus- or sulfur-containing acids, those acids themselves, etc., but not HF), adsorptive binding of the catalyst and subsequent separation by filtration, etc.

Following deactivation of the catalyst, the unconverted monomer and any solvent used concomitantly can be separated off by means of any known separation techniques such as, for example, distillation, optionally in the specific form of thin-layer distillation, extraction or crystallisation/filtration. Combinations of two or more of these techniques can, of course, also be used.

If the polyisocyanate prepared according to the invention is still to contain free, unconverted monomer, as is of interest, for example, for further processing to NCO-blocked products, separation of the monomers following deactivation of the catalyst can be omitted.

The unconverted monomer is preferably separated off. After separation, the products according to the invention preferably have a residual monomer content <0.5%, preferably <0.1 wt. %.

The unconverted monomer is preferably separated off by distillation.

As compared with catalysis by means of quaternary phosphonium salts which contain aryl and/or straight-chained alkyl groups on the P atom, for example triphenyl-butyl-, tetra-n-butyl- or tetra-n-octyl-phosphonium salts (see comparison examples), a markedly improved catalyst life—which does not decline as sharply as with the above-mentioned compounds of the prior art—is observed in the process according to the invention under otherwise identical reaction conditions, and this is verified in the examples and comparison examples by the turnover frequency (TOF). The latter is defined, based on the amount of NCO groups converted in the oligomerisation A, the amount of catalyst required therefor B and the reaction time t, according to the following equation:

$$TOF=A*(B*t)^{-1}[mol*(mol*sec)^{-1}].$$

According to a particular, continuous embodiment of the process according to the invention, the oligomerisation can be carried out in a tubular reactor or a multi-vessel cascade. In this case, advantage is gained in particular from the significantly lower tendency of the catalysts according to the invention, as compared with the known catalysts of the prior art, spontaneously to form gel particles in the product even when applied in a highly concentrated solution or in the form of the pure active ingredient.

Accordingly, the products and product mixtures obtainable by the process according to the invention are starting materials which can be used in many ways for the production of foamed and unfoamed plastics as well as surface coatings, coating compositions, adhesives and additives.

The process products according to the invention can be used in pure form or in conjunction with other isocyanate derivatives of the prior art, such as, for example, polyisocyanates containing uretdione, biuret, allophanate, isocyanurate and/or urethane groups, the free NCO groups of which have optionally been deactivated with blocking agents.

The comparison examples and examples which follow are intended to explain the invention in greater detail without limiting it.

All the references described above are incorporated by reference in their entireties for all useful purposes.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

EXAMPLES

All percentages are to be understood as being percent by weight, unless indicated otherwise.

Mol % were determined by NMR spectroscopy and are always based, unless indicated otherwise, on the sum of the NCO secondary products. Measurements were carried out using DPX 400 and DRX 700 devices from Brucker on approximately 5% ($^1$H-NMR) and approximately 50% ($^{13}$C-NMR) samples in dry $C_6D_6$ at a frequency of 400 and 700 MHz ($^1$H-NMR) or 100 and 176 MHz ($^{13}$C-NMR). As reference for the ppm scale there were used small amounts of tetramethylsilane in the solvent with 0 ppm $^1$H-NMR chem. shift. Alternatively, reference was made to the signal of the $C_6D_5H$ contained in the solvent: 7.15 ppm $^1$H-NMR chem. shift, 128.02 ppm $^{13}$C-NMR chem. shift. Data for the chemical shift of the compounds in question were taken from the literature (see D. Wendisch, H. Reiff and D. Dieterich, Die Angewandte Makromolekulare Chemie 141, 1986, 173-183 and literature cited therein, as well as EP-A 96 009).

The dynamic viscosities were determined at 23° C. using a VT 550 viscometer from Haake. By means of measurements at different shear rates it was ensured that the flow behaviour of the described polyisocyanate mixtures according to the invention as well as that of the comparison products corresponds to that of ideal Newtonian fluids. Mention of the shear rate can therefore be omitted.

The residual monomer contents were determined by gas chromatography.

Unless indicated otherwise, all reactions were carried out under a nitrogen atmosphere.

The diisocyanates used are products from Bayer MaterialScience AG, D-51368 Leverkusen, all other commercially available chemicals were obtained from Aldrich, D-82018 Taufkirchen.

The catalysts were obtained by methods known in the literature according to Scheme 1.

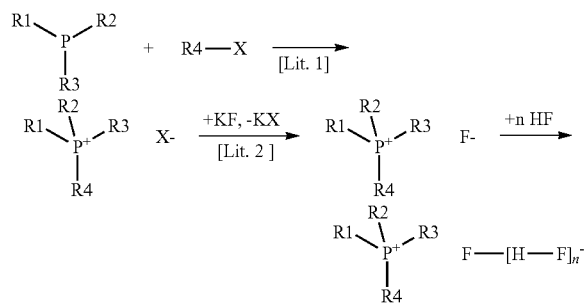

Lit. 1: K. Jödden in Methoden der Organischen Chemie (Houben Weyl) Volume E1, p. 495 ff and literature cited therein; Lit. 2: S. Dermeik and Y. Sasson, *J. Org. Chem.* 54 1989, 4827-4829 and literature cited therein.

Examples 1a to 1d

Comparison Examples

1a) Catalyst: triphenyl-n-butylphosphonium (hydrogen) difluoride (R1-R3=Ph, R4=n-Bu; n=1)

1b) Catalyst: tetra-n-butylphosphonium (hydrogen) difluoride (R1-R4=n-Bu; n=1)

1c) Catalyst: tetra-n-butylphosphonium (dihydrogen) trifluoride (R1-R4=n-Bu; n=2)

1d) Catalyst: tetra-n-octylphosphonium (hydrogen) difluoride (R1-R4=n-Oct; n=1)

1000 g of HDI were placed in a twin-walled flat-ground vessel adjusted to the desired starting temperature by an external circuit and equipped with a stirrer, with a reflux condenser connected to an inert gas installation (nitrogen/vacuum) and with a thermometer, and freed of dissolved gases by stirring for one hour in vacuo (0.1 mbar). After aeration with nitrogen, the amount of catalyst (as a 70% solution in isopropanol) indicated in Table 1 was metered in such a manner that the maximum temperature indicated in Table 1 was not exceeded. After 1 mol of NCO groups had been converted, the catalyst was deactivated by addition of an amount, equivalent to the catalyst, of p-toluenesulfonic acid (as a 40% solution in isopropanol); stirring was then carried out for a further 30 minutes at the reaction temperature, followed by working up. The time between the first addition of catalyst and addition of the deactivator solution was used to calculate the TOP (turnover frequency, [mol converted NCO groups/(mol catalyst*reaction time in seconds)]) indicated in Table 1.

Working up was carried out by vacuum distillation in a thin-layer evaporator, short-path evaporator (SPE) type, with an upstream pre-evaporator (PE) (distillation data: pressure: 0.08+/−0.04 mbar, PE temperature: 120° C., HV temp.: 140° C.), unconverted monomer being separated off as the distillate and the low-monomer polyisocyanate resin as the bottom product (starting flow: Example 1-0). The polyisocyanate resin was analysed, results see Table 2, and the distillate was collected in a second flat-ground stirring apparatus, identical in construction to the first, and made up to the starting amount (1000 g) with freshly degassed HDI. Then catalysis was carried out again and the procedure described at the beginning was followed. This procedure was repeated several times, the reaction temperature being varied. The results are to be found in Table 1.

In the case of the catalyst substituted partly by phenyl groups, the reaction was not carried out at a reaction temperature higher than 60° C. because decomposition of the catalyst proceeded so rapidly, even at 60° C., that unacceptably large amounts of catalyst were required to maintain the reaction to the desired conversion (here: 1 mol of NCO groups). However, even in the case of the phosphonium salts substituted solely by alkyl groups, a significant reduction in the catalytic activity, recognisable by the lower TOF values, is to be noted at higher reaction temperatures.

TABLE 1

| Example | Catalyst | | Reaction temperature [° C.] | | |
|---|---|---|---|---|---|
| No. | cation | anion | Start | Max. | TOF |
| 1a- A | n-Bu(Ph)$_3$P$^+$ | [HF$_2$]$^-$ | 60 | 64 | 0.007 |
| 1a- B | n-Bu(Ph)$_3$P$^+$ | [HF$_2$]$^-$ | 60 | 65 | 0.005 |
| 1b- A | n-Bu$_4$P$^+$ | [HF$_2$]$^-$ | 60 | 62 | 0.61 |
| 1b- B | n-Bu$_4$P$^+$ | [HF$_2$]$^-$ | 60 | 63 | 0.96 |
| 1b- C | n-Bu$_4$P$^+$ | [HF$_2$]$^-$ | 80 | 84 | 0.42 |
| 1b- D | n-Bu$_4$P$^+$ | [HF$_2$]$^-$ | 100 | 105 | 0.11 |
| 1b- E | n-Bu$_4$P$^+$ | [HF$_2$]$^-$ | 120 | 127 | 0.05 |
| 1b- F | n-Bu$_4$P$^+$ | [HF$_2$]$^-$ | 140 | 152 | 0.04 |
| 1c- A | n-Bu$_4$P$^+$ | [H$_2$F$_3$]$^-$ | 60 | 62 | 0.74 |
| 1c- B | n-Bu$_4$P$^+$ | [H$_2$F$_3$]$^-$ | 60 | 65 | 1.04 |

TABLE 1-continued

| Example | | Catalyst | | Reaction temperature [° C.] | | |
|---|---|---|---|---|---|---|
| No. | | cation | anion | Start | Max. | TOF |
| 1c- | C | n-Bu$_4$P$^+$ | [H$_2$F$_3$]$^-$ | 80 | 81 | 0.43 |
| 1c- | D | n-Bu$_4$P$^+$ | [H$_2$F$_3$]$^-$ | 100 | 107 | 0.09 |
| 1c- | E | n-Bu$_4$P$^+$ | [H$_2$F$_3$]$^-$ | 120 | 121 | 0.06 |
| 1c- | F | n-Bu$_4$P$^+$ | [H$_2$F$_3$]$^-$ | 140 | 140 | 0.05 |
| 1d- | A | n-Oct$_4$P$^+$ | [HF$_2$]$^-$ | 60 | 62 | 0.48 |
| 1d- | B | n-Oct$_4$P$^+$ | [HF$_2$]$^-$ | 60 | 36 | 0.73 |
| 1d- | C | n-Oct$_4$P$^+$ | [HF$_2$]$^-$ | 80 | 34 | 0.32 |
| 1d- | D | n-Oct$_4$P$^+$ | [HF$_2$]$^-$ | 100 | 34 | 0.27 |
| 1d- | E | n-Oct$_4$P$^+$ | [HF$_2$]$^-$ | 120 | 34 | 0.08 |
| 1d- | F | n-Oct$_4$P$^+$ | [HF$_2$]$^-$ | 140 | 34 | 0.03 |

Example 2 According to the Invention

Catalyst: n-butyl-tricyclopentylphosphonium (hydrogen) difluoride

The procedure described at the beginning was followed, except that a 40% n-butyl-tricyclopentylphosphonium (hydrogen) difluoride solution in isopropanol was used as catalyst. The results are to be found in Table 2.

TABLE 2

| Example | | Reaction temperature [° C.] | | |
|---|---|---|---|---|
| No. | | Start | Max. | TOF |
| 2- | A | 60 | 64 | 2.14 |
| 2- | B | 60 | 68 | 3.12 |
| 2- | C | 80 | 99 | 6.45 |
| 2- | D | 100 | 109 | 3.67 |
| 2- | E | 120 | 134 | 1.47 |
| 2- | F | 140 | 155 | 1.09 |
| 2- | G | 30 | 35 | 1.78 |

Example 3 According to the Invention

Catalyst: n-butyl-tricyclopentylphosphonium (dihydrogen) trifluoride

The procedure described in Comparison Example 1 was followed, except that a 45% n-butyl-tricyclopentylphosphonium (dihydrogen) trifluoride solution in isopropanol was used as catalyst. The results are to be found in Table 3.

TABLE 3

| Example | | Reaction temperature [° C.] | | |
|---|---|---|---|---|
| No. | | Start | Max. | TOF |
| 3- | 0 | 60 | 64 | 2.41 |
| 3- | A | 60 | 68 | 3.22 |
| 3- | B | 80 | 84 | 7.36 |
| 3- | C | 100 | 105 | 4.22 |

Example 4 According to the Invention

Catalyst: n-butyl-tricyclohexylphosphonium (hydrogen) difluoride

The procedure described in Comparison Example 1 was followed, except that a 20% n-butyl-tricyclohexylphosphonium (hydrogen) difluoride solution in isopropanol/diethylene glycol dimethyl ether (1:3.3) was used as catalyst. The results are to be found in Table 3.

TABLE 4

| Example | | Reaction temperature [° C.] | | |
|---|---|---|---|---|
| No. | | Start | Max. | TOF |
| 4- | A | 60 | 65 | 1.98 |
| 4- | B | 60 | 63 | 2.25 |
| 4- | C | 80 | 90 | 4.42 |
| 4- | D | 100 | 105 | 4.56 |
| 4- | E | 120 | 139 | 4.89 |
| 4- | F | 140 | 149 | 1.42 |

Example 5 According to the Invention

Catalyst: di-n-butyl-dicyclopentylphosphonium (hydrogen) difluoride

The procedure described in Comparison Example 1 was followed, except that a 50% di-n-butyl-dicyclopentylphosphonium (hydrogen) difluoride solution in isopropanol was used as catalyst. The results are to be found in Table 5.

TABLE 5

| Example | | Reaction temperature [° C.] | | |
|---|---|---|---|---|
| No. | | Start | Max. | TOF |
| 5- | A | 60 | 61 | 1.15 |
| 5- | B | 60 | 61 | 1.96 |
| 5- | C | 80 | 83 | 1.08 |
| 5- | D | 100 | 103 | 0.52 |
| 5- | E | 120 | 128 | 0.35 |
| 5- | F | 140 | 146 | 0.11 |

Example 6 According to the Invention

Catalyst: tri-n-hexyl-cyclohexylphosphonium (hydrogen) difluoride

The procedure described in Comparison Example 1 was followed, except that a 90% tri-n-hexyl-cyclohexylphosphonium (hydrogen) difluoride solution in isopropanol was used as catalyst. The results are to be found in Table 6.

TABLE 6

| Example | | Reaction temperature [° C.] | | |
|---|---|---|---|---|
| No. | | Start | Max. | TOF |
| 6- | 0 | 60 | 62 | 0.77 |
| 6- | A | 60 | 62 | 1.11 |
| 6- | B | 100 | 107 | 0.83 |
| 6- | C | 140 | 145 | 0.18 |

Examples 7 and 8

Comparison Examples

Catalyst: Tetra-n-Butylphosphonium (Hydrogen) Difluoride

And 9 and 10 According to the Invention

Catalyst: n-Butyl-Tricyclopentylphosphonium (Hydrogen) Difluoride

The procedure described in Comparison Example 1 was followed, except that IPDI was used instead of HDI and the conversion of NCO groups was adjusted to about 2 mol. At a reaction temperature of 60° C. (Comparison Example 7), a TOF of from 0.002 to 0.005 was obtained. If the reaction temperature is raised to 100° C. (Comparison Example 8), it is not possible to achieve a uniform reaction procedure despite the continuous addition of catalyst. After 1.26 mol of NCO groups had been converted, the TOF was 0.0005.

In reactions carried out analogously to Comparison Examples 7 and 8 using the catalyst from Example 2 (single addition), the following were obtained:
60° C. (Example 9): TOF in the range from 0.02 to 0.06
100° C. (Example 10): TOF about 0.01

The invention claimed is:

1. A process which comprises reacting
  a) at least one organic isocyanate having an NCO functionality greater than or equal to 1,
  b) a catalyst comprising at least one phosphonium salt comprising at least one cycloalkyl substituent bonded directly to a P atom of a phosphonium cation,
  c) optionally a solvent, and
  d) optionally additives,
  wherein the phosphonium salt comprises a cation corresponding to the formula I:

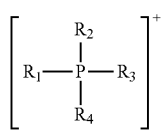

Formula I wherein $R_1$ to $R_4$ independently of one another represent organic radicals selected from the group consisting of $C_1$- to $C_{20}$-alkyl which is optionally branched, cyclopentyl, and cyclohexyl which is optionally substituted, and wherein at least two of the radicals $R_1$ to $R_4$ represent an optionally substituted cyclopentyl, cyclohexyl radical, or combinations thereof which are each bonded directly to the P atom via a ring carbon atom, and wherein the phosphonium cation of the formula (I) has a counter-ion $X^-$ wherein $X^-$ is selected from the group consisting of di- and poly-(hydrogen) fluoride ($[F^- \times (HF)_m]$, wherein m represents whole or fractional numbers from 0.001 to 20.

2. The process according to claim 1, wherein the at least one organic isocyanate is selected from the group consisting of aliphatic di- or poly-isocyanates, cycloaliphatic di- or poly-isocyanates, araliphatic di- or poly-isocyanates, and mixtures thereof, and wherein the at least one organic isocyanate has a functionality greater than or equal to 2.

3. The process according to claim 1, wherein the reaction is carried out at a temperature from 0 to 250° C.

4. The process according to any claim 1, further comprising terminating the reaction when from 5 to 80% of the at least one organic isocyanate has been converted.

5. The process according to claim 1, further comprising separating the unconverted isocyanates from the reaction mixture.

6. A isocyanate produced by a process comprising reacting
  a) at least one organic isocyanate having an NCO functionality greater than or equal to 1,
  b) a catalyst comprising at least one phosphonium salt comprising at least one cycloalkyl substituent bonded directly to a P atom of a phosphonium cation,
  c) optionally a solvent, and
  d) optionally additive,
  wherein the phosphonium salt comprises a cation corresponding to the formula I:

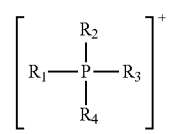

Formula I wherein $R_1$ to $R_4$ independently of one another represent organic radicals selected from the group consisting of $C_1$- to $C_{20}$-alkyl which is optionally branched, cyclopentyl, and cyclohexyl which is optionally substituted, and wherein at least two of the radicals $R_1$ to $R_4$ represent an optionally substituted cyclopentyl, cyclohexyl radical, or combinations thereof which are each bonded directly to the P atom via a ring carbon atom,
  wherein the phosphonium cation of the formula (I) has a counter-ion $X^-$ wherein $X^-$ is selected from the group consisting of di- and poly-(hydrogen) fluoride ($[F^- \times (HF)_m]$, wherein m represents whole or fractional numbers from 0.001 to 20.

7. The isocyanate according to claim 6, wherein the at least one organic isocyanate is selected from the group consisting of aliphatic di- or poly-isocyanates, cycloaliphatic di- or poly-isocyanates, araliphatic di- or poly-isocyanates, and mixtures thereof, and wherein the at least one organic isocyanate has a functionality greater than or equal to 2.

8. The isocyanate according to claim 6, wherein the reaction is carried out at a temperature from 0 to 250° C.

9. The isocyanate according to claim 6, further comprising terminating the reaction when from 5 to 80% of the at least one organic isocyanate has been converted.

10. The isocyanate according to claim 6, further comprising separating the unconverted isocyanates from the reaction mixture.

* * * * *